(12) United States Patent
Suter et al.

(10) Patent No.: US 11,940,455 B2
(45) Date of Patent: Mar. 26, 2024

(54) CONSUMABLE MANAGEMENT SYSTEM FOR LABORATORIES

(71) Applicant: Roche Diagnostics Operations, Inc., Indianapolis, IN (US)

(72) Inventors: Urs Suter, Zurich (CH); Riccardo Leone Benedetti, Fehraltorf (CH); Gregor Hotz, Zug (CH); Oliver Rusterholz, Kuenten (CH); Robert Theiler, Stallikon (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 355 days.

(21) Appl. No.: 16/565,689

(22) Filed: Sep. 10, 2019

(65) Prior Publication Data

US 2020/0096526 A1  Mar. 26, 2020

(30) Foreign Application Priority Data

Sep. 20, 2018 (EP) .................................... 18195680

(51) Int. Cl.
*G01N 35/00* (2006.01)
*G16H 10/40* (2018.01)

(52) U.S. Cl.
CPC ....... *G01N 35/00663* (2013.01); *G16H 10/40* (2018.01); *G01N 2035/00673* (2013.01); *G01N 35/00732* (2013.01); *G01N 2035/00881* (2013.01)

(58) Field of Classification Search
CPC ....... G01N 35/00663; G01N 35/00732; G01N 2035/00673; G01N 2035/00881; G16H 10/40; G16H 40/20; B65G 1/1371; G06Q 10/087; G06Q 50/28; G06Q 10/08; G06K 17/0029

See application file for complete search history.

(56) References Cited

U.S. PATENT DOCUMENTS

| | | | |
|---|---|---|---|
| 6,464,142 | B1 | 10/2002 | Denenberg et al. |
| 8,318,499 | B2 | 11/2012 | Fritchie et al. |
| 9,076,120 | B2 | 7/2015 | Burri et al. |
| 10,163,223 | B2 | 12/2018 | Tachibana |

(Continued)

FOREIGN PATENT DOCUMENTS

| | | |
|---|---|---|
| AU | 2012305682 B2 | 8/2015 |
| CN | 105006073 A | 10/2015 |

(Continued)

OTHER PUBLICATIONS

TECCO Wearable RFID reader, http://www.go-v.co.jp/tecco/en/, 3 pp.

(Continued)

*Primary Examiner* — Jill A Warden
*Assistant Examiner* — John McGuirk
(74) *Attorney, Agent, or Firm* — Taft Stettinius & Hollister LLP

(57) ABSTRACT

A consumable management system comprising a consumable storage cluster with a plurality of storage compartments is presented. Each storage compartment is configured to receive one or more consumables. The consumable management system further comprises storage compartment indicators to provide guidance to a user and a detection unit for validating user action(s).

20 Claims, 5 Drawing Sheets

(56) References Cited

U.S. PATENT DOCUMENTS

| | | |
|---|---|---|
| 10,837,974 B2 | 11/2020 | Postma et al. |
| 2003/0099573 A1 | 5/2003 | Tseung et al. |
| 2004/0135905 A1 | 7/2004 | Suda |
| 2006/0263268 A9* | 11/2006 | Tseung ............... B65D 1/0223 422/510 |
| 2009/0134978 A1 | 5/2009 | Imai |
| 2009/0173779 A1* | 7/2009 | Szesko ................ G16H 20/13 235/375 |
| 2011/0212859 A1 | 9/2011 | Obanion et al. |
| 2013/0159135 A1 | 6/2013 | Jones et al. |
| 2014/0110480 A1* | 4/2014 | Burri ..................... B01L 9/56 235/385 |
| 2014/0236615 A1 | 8/2014 | Ragusky et al. |
| 2014/0297487 A1* | 10/2014 | Bashkin ............... E05B 65/46 705/28 |
| 2015/0186834 A1 | 7/2015 | Mickles et al. |
| 2018/0003600 A1* | 1/2018 | Neef ............... G01N 35/00732 |

FOREIGN PATENT DOCUMENTS

| | | |
|---|---|---|
| CN | 205540826 U | 8/2016 |
| JP | 2011209275 A | 10/2011 |
| JP | 2014085349 A | 5/2014 |
| JP | 2014-199202 A | 10/2014 |
| JP | 2017026465 A | 2/2017 |
| WO | 2013/036941 A2 | 3/2013 |
| WO | 2013/170204 A1 | 11/2013 |
| WO | 2016136435 A1 | 9/2016 |

OTHER PUBLICATIONS

Search Report; National Intellectual Property Administration, P.R. China; Chinese Application No. 201910885813.6; dated Oct. 12, 2023; 3 pages.

Office Action; Japanese Patent Office; Japanese Application No. 2019-170182; dated Jul. 7, 2023; 11 pages.

* cited by examiner

CONSUMABLE MANAGEMENT SYSTEM FOR LABORATORIES

CROSS-REFERENCE TO RELATED APPLICATIONS

This application claims priority to EP 18195680.6, filed Sep. 20, 2018 which is hereby incorporated by reference.

BACKGROUND

The present disclosure generally relates to a consumable management system for laboratories, a method for operating a consumable management system and a computer program product comprising instructions which, when executed by a computer system, cause a consumable management system to perform the method for operating a consumable management system.

In vitro diagnostic testing has a major effect on clinical decisions, providing physicians with pivotal information. Particularly, there is great emphasis on providing quick and accurate test results in critical care settings.

Diagnostic testing makes use of various consumables such as reagents, system fluids, quality control material, calibrator materials, microplates/microwell plates, reaction vessels, measurement cuvettes, sample tubes, pipetting tips, and the like. In order to be able to carry out laboratory tests, it is therefore important that laboratories have all required consumables available.

In order to reduce the risk of running out of consumables, currently laboratories increase their stock to cover even more than the expected need for a particular consumable in an attempt to buffer unpredictable situations.

However, storage space needs to be used to its utmost efficiency as it is coupled with both set-up and recurring costs. This applies even more in case of storage of consumables such as reagents which need to be kept in a defined temperature range, e.g. in a refrigerator. Furthermore, a stock that constantly exceeds the demand/usage (by a safety margin) inevitably leads to waste, as most of the consumables required for laboratory tests have a strict expiration date or shelf life. In addition, the stability of various consumables, in particular reagents, quality control/calibrator material, is limited after opening.

Therefore, there is a need for a consumable management system which ensures that consumable(s) are available for all required laboratory tests while avoiding use of unnecessary storage space or waste consumables by having a too large reserve stock of consumables.

SUMMARY

According to the present disclosure, a method and system for consumable management for laboratories is presented. The consumable management system can comprise a consumable storage cluster comprising a plurality of storage compartments. Each storage compartment can be configured to receive one or more consumables. The consumable storage cluster can also comprise a plurality of compartment indicators. A compartment indicator can be associated with each storage compartment and configured to indicate one of the plurality of storage compartments to a user. The consumable management system can also comprise a control unit communicatively connected to a database for maintaining an inventory of consumables stored in the plurality of storage compartments, a detection unit communicatively connected with the control unit and configured to detect removal and replenishment of consumables from and into the storage compartments and signaling the removal and replenishment to the control unit, and an interface communicatively connected with the control unit for receiving an input indicative of a consumable demand and/or consumable replenishment intent. The control unit can be configured to: determine a particular consumable to be retrieved in accordance with the consumable demand and the inventory of consumables, determine the storage compartment holding the particular consumable to be retrieved and control the plurality of compartment indicators and control the plurality of compartment indicators to indicate the storage compartment holding the particular consumable to be retrieved, determine the particular storage compartment best suited to receive the consumable replenishment and control the plurality of compartment indicators to indicate the storage compartment best suited to receive a consumable replenishment, process signals from the detection unit in order to validate removal of the particular consumable from the storage compartment indicated and replenishment into the storage compartment indicated, generate an alert signal upon failure of the validation of the removal of the particular consumable from the storage compartment indicated and replenishment into the storage compartment indicated, and process signals from the detection unit in order to update the inventory of consumables upon removal and upon replenishment of consumables.

Accordingly, it is a feature of the embodiments of the present disclosure to provide for a consumable management system which ensures that consumable(s) are available for all required laboratory tests while avoiding use of unnecessary storage space or waste consumables by having a too large reserve stock of consumables. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1:
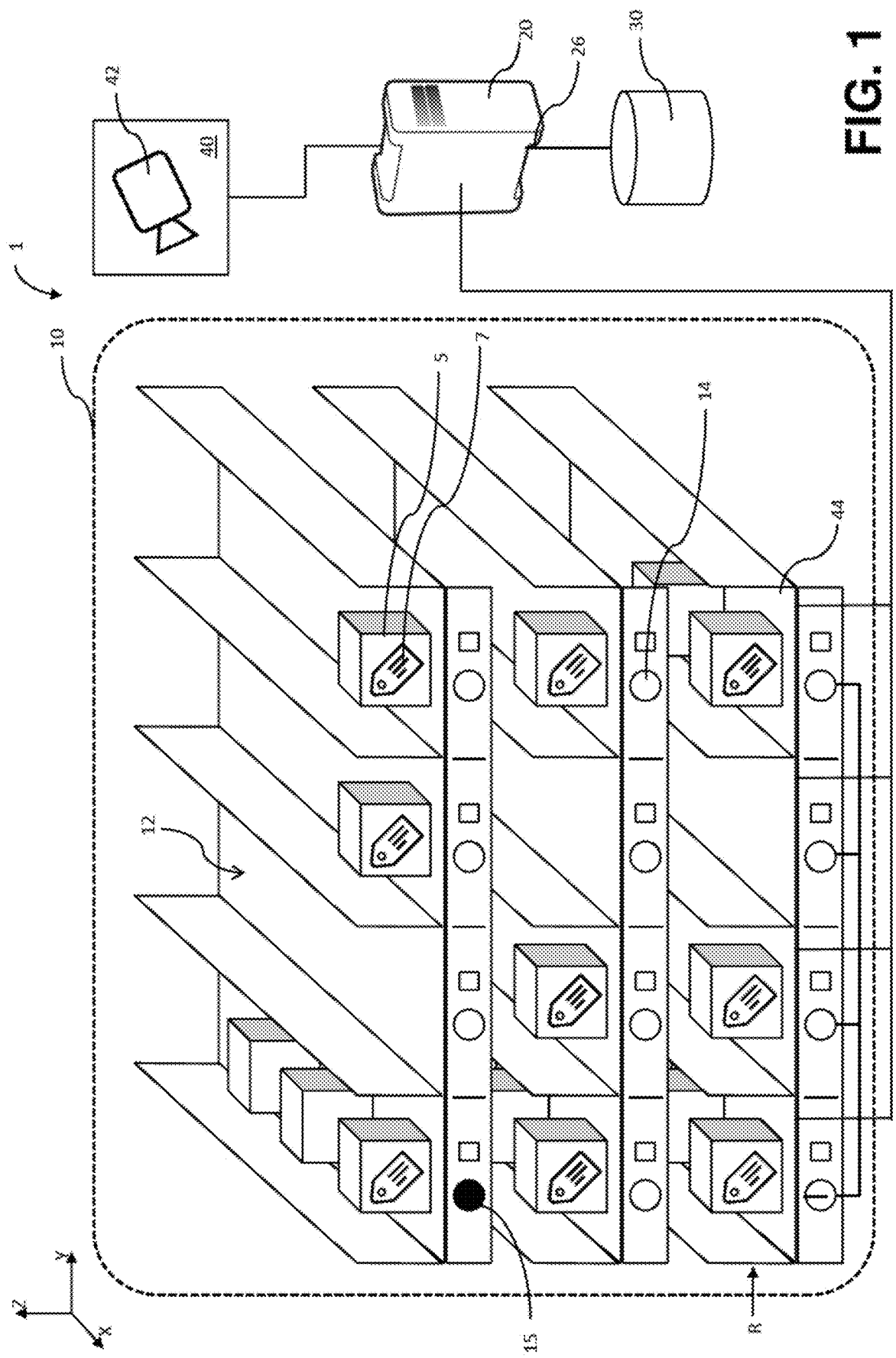
FIG. 1 illustrates a schematic diagram of a first embodiment of the disclosed consumable management system according to the present disclosure.

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

In addition, certain terms will be used in this patent application, the formulation of which should not be interpreted to be limited by the specific term chosen, but as to relate to the general concept behind the specific term.

As used herein, the terms 'comprises,' 'comprising,' 'includes,' 'including,' 'has,' 'having' or any other variation thereof, are intended to cover a non-exclusive inclusion of features.

The term 'laboratory instrument' as used herein can encompass any apparatus or apparatus component operable to execute one or more processing steps/workflow steps on one or more biological samples and/or one or more reagents. The expression 'processing steps' thereby can refer to physically executed processing steps such as centrifugation, aliquotation, analyte isolation, sample analysis and the like. The term 'instrument' can cover pre-analytical instruments, post-analytical instruments and also analytical instruments.

The term 'analyzer'/'analytical instrument' as used herein can encompasses any apparatus or apparatus component configured to obtain a measurement value. An analyzer can be operable to determine via various chemical, biological, physical, optical or other technical procedures a parameter value of the sample or a component thereof. An analyzer may be operable to measure the parameter of the sample or of at least one analyte and return the obtained measurement value. The list of possible analysis results returned by the analyzer can comprise, without limitation, concentrations of the analyte in the sample, a digital (yes or no) result indicating the existence of the analyte in the sample (corresponding to a concentration above the detection level), optical parameters, DNA or RNA sequences, data obtained from mass spectroscopy of proteins or metabolites and physical or chemical parameters of various types. An analytical instrument may comprise units assisting with the pipetting, dosing, and mixing of samples and/or reagents. The analyzer may comprise a reagent holding unit for holding reagents to perform the assays. Reagents may be arranged for example in the form of containers or cassettes containing individual reagents or group of reagents, placed in appropriate receptacles or positions within a storage compartment or conveyor. It may comprise a consumable feeding unit or consumable loading and unloading unit. The analyzer may comprise a process and detection system whose workflow can be optimized for certain types of analysis. Examples of such analyzer can be clinical chemistry analyzers, coagulation chemistry analyzers, immunochemistry analyzers, urine analyzers, nucleic acid analyzers, used to detect the result of chemical or biological reactions or to monitor the progress of chemical or biological reactions.

The term 'communication network' as used herein can encompass any type of wireless network, such as a WiFi™, GSM™, UMTS or other wireless digital network or a cable based network, such as Ethernet™ or the like. In particular, the communication network can implement the Internet protocol (IP). For example, the communication network can comprise a combination of cable-based and wireless networks.

The term 'control unit' as used herein can encompass any physical or virtual data processing device. In some embodiments, the control unit may be integral with a data management unit, may be comprised by a server computer and/or be part of one laboratory instrument or even distributed across multiple instruments of the laboratory system. The control unit may, for instance, be embodied as a programmable logic controller running a computer-readable program provided with instructions to perform operations. A 'data management unit' can be a computing unit for storing and managing data. This may involve data relating to consumable(s) required to carry out processing step(s) on biological samples. The data management unit may be connected to an LIS (laboratory information system) and/or an HIS (hospital information system). The data management unit (DMU) can be a unit within or co-located with an automated system. It may be part of the control unit. Alternatively, the DMU may be a unit remotely located. For instance, it may be embodied in a computer connected via a communication network.

The term 'interface' as used herein can encompass any suitable piece of software and/or hardware for interactions between an operator and a machine or a machine and another machine including but not limited to a graphical user interface for receiving as input a command from an operator and also to provide feedback and convey information thereto. Also, a system/device may expose several interfaces to serve different kinds of users/operators.

The term 'reagent' as used herein can refer to materials necessary for performing an analysis of analytes, including reagents for sample preparation, control reagents, reagents for reacting with the analyte to obtain a detectable signal, and/or reagents necessary for detecting the analyte. Such reagents may include reagents for isolating an analyte and/or reagents for processing a sample and/or reagents for reacting with an analyte to obtain a detectable signal and/or washing reagents and/or diluents.

The term 'reagent cassette' as used herein can refer to any vessel/container comprising a liquid or suspension of reagents. Alternatively, a reagent cassette can be a holder for holding container(s) comprising a liquid or a suspension of reagents.

As used herein, the term 'calibrator' can refer to a composition containing a known concentration of an analyte for use in determining the concentration of the analyte in a sample containing an unknown concentration of the analyte. The term 'quality control' (QC) materials as used herein can refer to any composition with known concentration of an analyte, such as positive and negative controls, that serve the purpose of providing evidence that an analytical test is successfully performed and is giving the expected level of sensitivity and specificity as characterized during technical optimization and validation of the analytical test for diagnostic use. In other words, a 'quality control' can be used in the present disclosure as referring to a physical sample used in one or several monitoring processes to monitor the performance of particular tests or assays of an analyzer. Positive controls primarily can monitor calibration of the system and sensitivity. Negative controls can be primarily used to evaluate the specificity of the analytical tests to identify false-positive results.

The term 'RFID reader as used herein can include devices that can read information from and/or write information into an RFID tag. Typically, RFID readers can include a coil or antenna and circuitry to transmit and receive signals with the coil or antenna. The RFID reader antenna can generate an electromagnetic field, thereby transferring energy to the tag. Depending on the design of the tag, a portion of the energy transferred to the tag can be reflected to the reader so as to provide information about the tag back to the reader. Some RFID systems can be used to read and optionally write data to and from the RFID tag. RFID readers can generate signals spanning distances from less than one centimeter to more than fifty meters depending on frequency and power of the signals generated at the RFID reader antenna.

The term 'RFID tag' as used herein can refer to either an active or passive RFID tag that contains information. An RFID tag or transponder can include a coil or antenna and some information stored on an RFID chip that can be read and/or written by an RFID reader. Correspondingly, the RFID tag can be read only or read/write and the information associated with the RFID tag can be hard-coded into the RFID tag at the time of manufacture or at some later time. Typically, RFID tags can be categorized as either active or passive. Active RFID tags can be powered by an internal battery and can be typically read/write, i.e., tag data can be rewritten and/or modified. An active tag's memory size can vary according to application requirements, some systems operating with up to 1 MB of memory and more. Passive RFID tags can operate without a separate external power source and obtain operating power generated from the reader. Passive tags can be consequently typically lighter than active tags, less expensive, and offer a long operational lifetime. Passive tags can typically have shorter read ranges than active tags and require a higher-powered reader. Read-only tags are typically passive and can be programmed with a unique set of data that can be typically predetermined at the time of manufacture of the tag. It is understood that passive read/write tags can also be employed consistent with the present teachings.

Disclosed herein is a consumable management system comprising a consumable storage cluster with a plurality of storage compartments, each storage compartment being configured to receive one or more consumables. The consumable management system further comprises a control unit communicatively connected to a database for maintaining an inventory of consumables stored in the plurality of storage compartments.

In order to capture consumable demand and/or consumable replenishment intent, the consumable management system can further comprise an interface for receiving an input indicative of a consumable demand and/or consumable replenishment intent.

In addition to maintaining an up to date and suitable inventory of consumables, the management of consumables in a laboratory can be significantly improved by a guided as well as validated removal and replenishment of consumables.

In one embodiment, a user can be provided guidance for the removal and replenishment of the consumables. User guidance can be achieved by a plurality of compartment indicators. A compartment indicator can be associated with each storage compartment and configured to indicate one of the plurality of storage compartments to a user.

In order to guide/support the user in identifying the right consumable for removal, the control unit can be configured to determine a particular consumable to be retrieved in accordance with the consumable demand and the inventory of consumables and to determine the storage compartment holding the particular consumable to be retrieved and control the plurality of compartment indicators such as to indicate the storage compartment holding the particular consumable to be retrieved.

In order to guide/support the user in replenishment of consumables, the control unit can be configured to determine the particular storage compartment best suited to receive the consumable replenishment and control the plurality of compartment indicators such as to indicate the storage compartment best suited to receive a consumable replenishment.

In one embodiment, removal and replenishment of the right consumable by the user can be validated. User actions (removal and replenishment) can be validated by way of detection unit communicatively connected to the control unit and configured to detect removal and replenishment of consumables from and into the storage compartments and signaling the removal and replenishment to the control unit. In one embodiment, detection of removal and replenishment of the right consumables from and into the storage compartments can be by identifiers attached to the consumables.

The control unit can further be configured to process signals from the detection unit in order to validate removal of the particular consumable from the storage compartment indicated and replenishment into the storage compartment indicated. In case the validation fails—meaning the wrong consumable has been removed or the consumable replenishment has been placed in the wrong storage compartment—the control unit can be configured to indicate an error/raise an alarm.

Embodiments disclosed herein can be advantageous as user guidance in combination with user action validation provides for an easier to use and significantly less error prone management of consumables. On one hand, guidance can provide significant usability improvement over known consumable management systems, allowing users to quickly and easily identify the location of the consumable based on the consumable demand and hence remove the right consumable. Furthermore, user guidance can improve the maintenance of a proper inventory by aiding users in placing consumable replenishment in the right storage compartment.

On the other hand, user action validation can ensure that the guidance can thus be easily detectable and rectifiable.

Referring initially to FIG. 1, FIG. 1 shows a schematic diagram of a first embodiment of the consumable management system 1. The consumable management system 1 can comprise a consumable storage cluster 10, a control unit 20, detection unit 40, and an interface 26.

According to some embodiments, the consumable storage cluster 10 can be or can be part of a refrigerator configured to keep consumables stored therein at a set temperature. The consumable storage cluster 10 can comprise a plurality of storage compartments 12. Each storage compartment 12 can be configured to receive one or more consumables 5. According to some embodiments, the storage compartments 12 can be arranged as a number of rows R arranged vertically on top of each other along the Z-direction of the three-dimensional Cartesian coordinate system, while each row comprising one or more storage compartments 12 side-by-side along the Y-direction of the three-dimensional Cartesian coordinate system. In one embodiment, the consumable storage cluster 10 can be arranged as a two-dimensional raster of rows and columns, such as a plurality of shelves, each with a plurality of sorted lanes arranged side-by-side.

The storage compartments 12 of the cluster 10 can be configured to receive one or more consumables 5. In one embodiments, the consumables 5 can be arranged in the storage compartments 12, one behind the other. While such an arrangement is common, side-by-side or other arrangements are conceivable. Furthermore, consumable storage clusters 10 can be conceivable wherein storage compartments 12 in a row are not physically separated, e.g., only marked by a delimiter line or the like.

The consumables 5 can comprise one or more of (but not limited to) reagent cassettes, quality control material, calibrator material, liquid handling consumables (such as pipettes, microwell plates), reaction cups, and the like.

Figure 2:
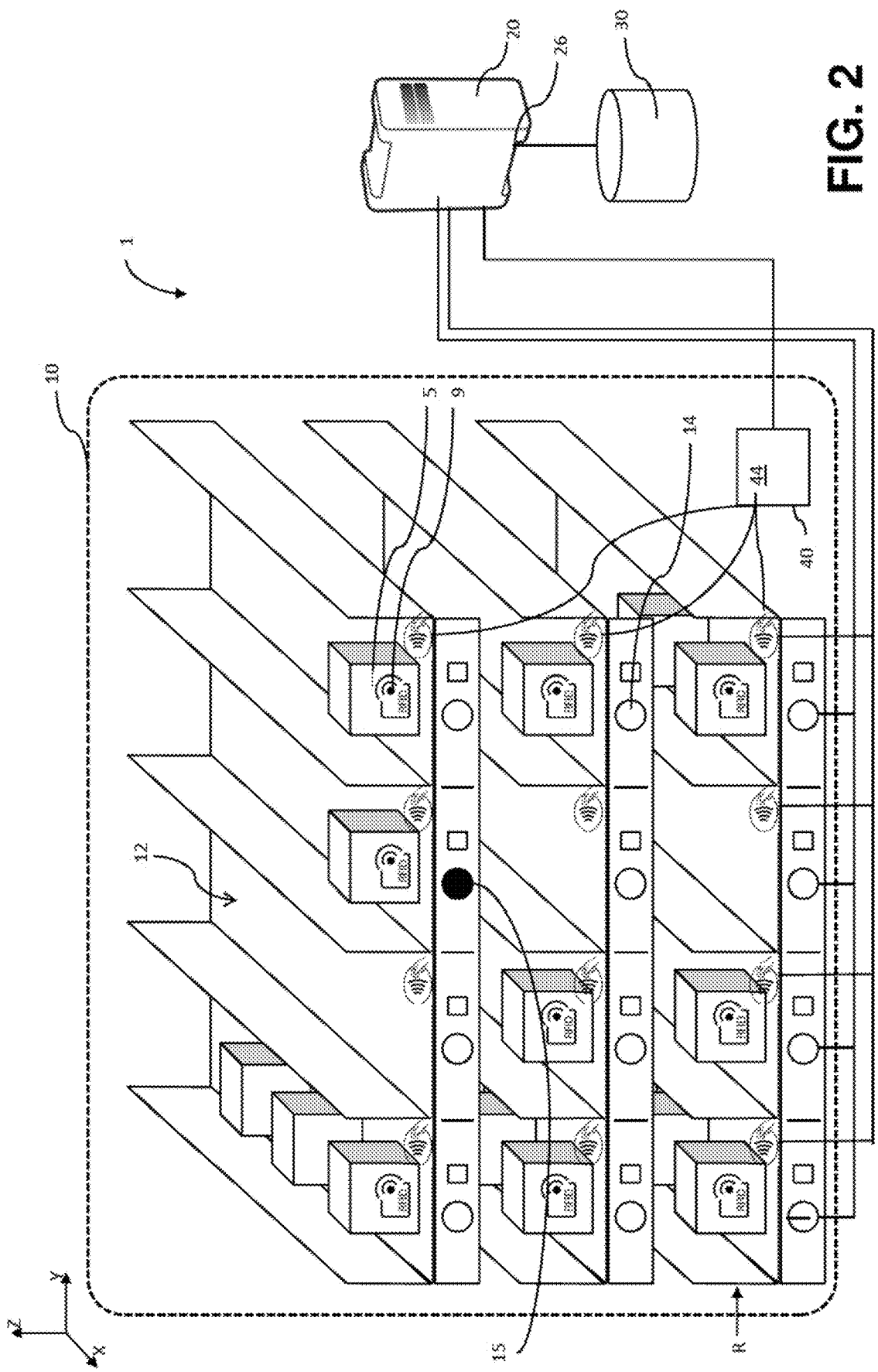
FIG. 2 illustrates a schematic diagram of a further embodiment of the disclosed consumable management system according to the present disclosure.

In order to provide user guidance, as shown on FIGS. 1 and 2, the consumable storage cluster 10 can further comprise a plurality of compartment indicators 14, a compartment indicator 14 being associated with each storage compartment 12 and configured to indicate one of the plurality of storage compartments 12 to a user. The term 'indicate' can refer to the act of providing an aid to a user to uniquely identify one particular storage compartment 12 within the cluster 10. According to some embodiments, the indication of a storage compartment 12 within the cluster 10 can be implemented as a visual indication. According to the embodiment of FIGS. 1 and 2, the plurality of compartment indicators 14 can comprise a plurality of light sources such as, for example, light emitting diodes (LEDs), as compartment indicators 14. Each light source can be arranged in the proximity of the respective storage compartment 12. When a particular compartment 12 is to be indicated, the corresponding light source can be activated (or can change color, blink, and the like) to visually attract the attention of a user and uniquely and unambiguously indicate one single storage compartment 12. According to some embodiments, the LEDs (acting as compartment indicators 14) can be arranged on LED strips and can be attached to a front panel of a drawer as an add-on solution, enabling retrofitting of existing consumable storage systems, thereby allowing a cost-effective solution for laboratories.

The consumable management system 1 can further comprise a control unit 20 communicatively connected to a database 30 for maintaining an inventory of consumables stored in the plurality of storage compartments 12. According to various embodiments, the database 30 can be a dedicated database for maintenance of consumable inventory. Alternatively, or additionally, the database 30 can be part of a laboratory information system (LIS) communicatively connected to and configured to manage a plurality of laboratory instruments. The inventory of consumables can comprise: a list of consumables stored in the consumable storage cluster 10 and the corresponding storage compartment 12 as well as the expiry date of consumables (which do have an expiry date). Furthermore, according to some embodiments, the inventory of consumables can comprise opening time and shelf life of consumables (time till expiry if opened) and remainder amount of partially used consumables.

In order to validate user actions, the consumable management system 1 can further comprise a detection unit 40 communicatively connected with the control unit 20. The detection unit 40 can be configured to detect removal and replenishment of consumables 5 from and into the storage compartments 12 and signaling the removal and replenishment to the control unit 20. Detection units 40 can operate on various principles (optical, radio frequency, and the like) to monitor user interaction with the consumable storage cluster 10 such as, for example, removal and replenishment of consumables 5.

FIG. 1 shows a first embodiment of the consumable management system 1, wherein the detection unit 40 can comprise an optical data acquisition device 42 such as a video camera. The optical data acquisition device 42 can be placed such as to capture images of the consumable storage cluster 10. Using an image processing, the optical data acquisition device 42 can be configured to detect the particular storage compartment(s) 12 from which consumables 5 can be removed and into which consumables 5 can be replenished.

Additionally, or alternatively, the acquisition device 42 can be arranged and configured such as to capture images of labels 7 attached to the consumables 5, reading data therefrom and detect whether the consumable 5 is being removed or replenished is the particular consumable 5 determined by the control unit 20 that must be removed/replenished. Data from labels 7 attached to the consumables 5 can comprise (but is not limited to): an identifier of the consumable 5, expiry date, lot number written in clear text or encoded as a barcode/QR code on the label 7. Based on such data from the label 7 read by the optical data acquisition device 42 of detection unit 40, the control unit 20 can maintain an inventory of consumables stored in the plurality of storage compartments 12.

FIG. 2 shows a further embodiment of the consumable management system 1, wherein the detection unit 40 can comprise a plurality of RFID tag readers 44. An RFID tag reader 44 can be associated with each storage compartment 12 and configured to read RFID tags 9 attached to consumables 5 removed from or replenished into the consumable storage cluster 10 such as to detect the particular storage compartment 12 from which consumables 5 are removed and into which consumables 5 are being replenished.

Furthermore, the consumable management system 1 can comprise an interface 26 communicatively connected with the control unit 20 for receiving an input indicative of a consumable demand and/or consumable replenishment intent. In other words, the interface 20 can inform the consumable management system 1 of a need for a certain consumable 5 and to inform the consumable management system 1 that a certain consumable 5 has been received and needs to be stored (replenished) therein. According to a first embodiment, the interface 26 can be an interface to a LIS providing data indicative of consumable demand of connected laboratory instruments. According to a further embodiment, the interface 26 can a user interface (such as a GUI) configured to receive manual input from a user, capturing the consumable demand and/or consumable replenishment intent. According to an even further embodiment, the interface 26 can be communicatively connected to a reader such as, for example, RFID or barcode, and/or the detection unit, in order to identify a consumable 5 ready to be replenished.

FIG. 2 also shows an embodiment of the detection unit 40 comprising a plurality of RFID tag readers 44. An RFID tag reader 44 can be associated with each storage compartment 12 and configured to read RFID tags 9 attached to consumables 5 being removed from or replenished into the consumable storage cluster 10 such as to detect the particular storage compartment 12 from which consumables 5 are removed and into which consumables 5 are being replenished. In this embodiment, the RFID tag readers 44 can each be configured such as to only read RFID tags 9 of consumables 5 within the corresponding compartment 12. This may be achieved for example by shielding compartments 12 against radio frequency cross-talk.

Figure 3:
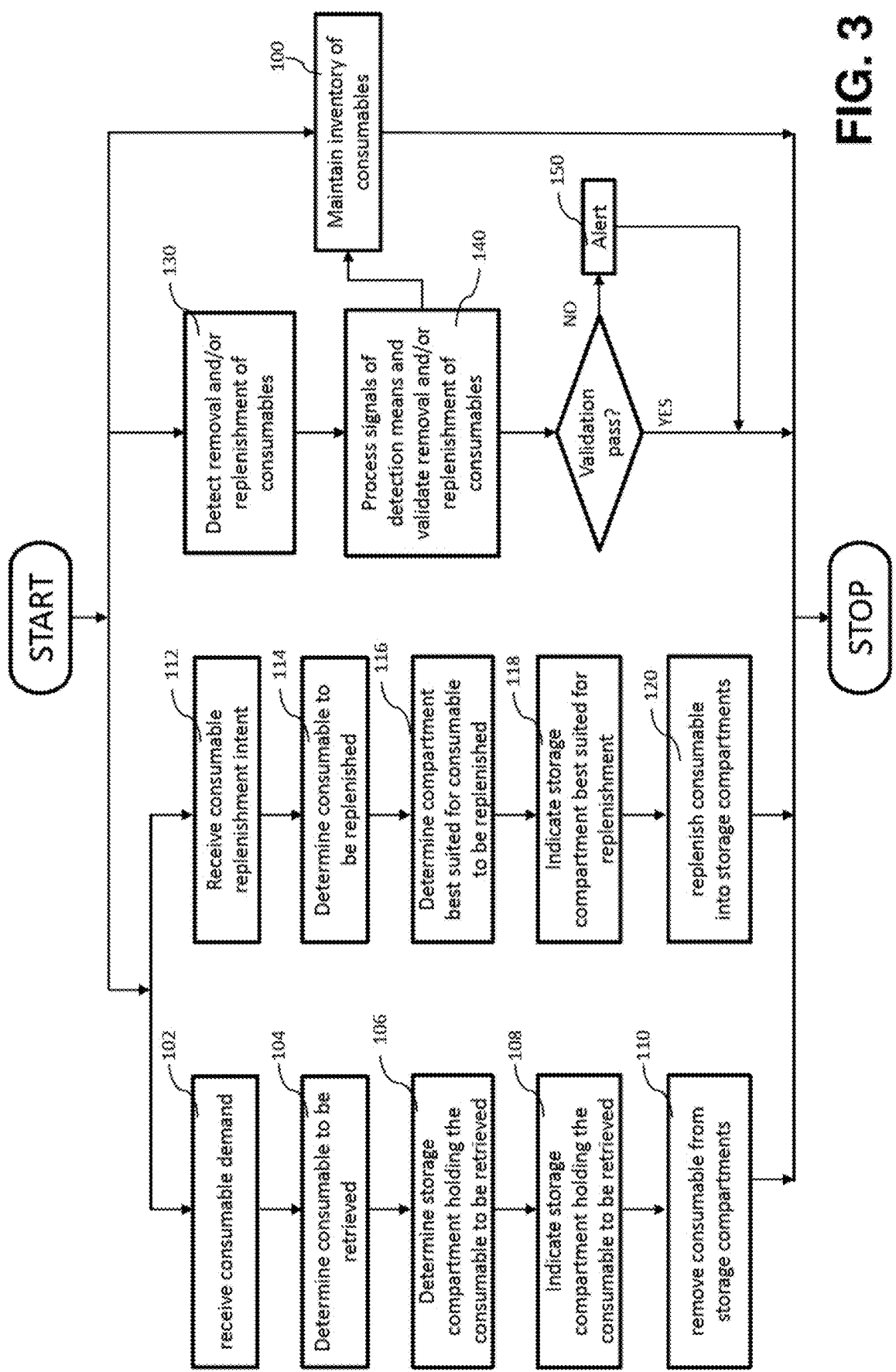
FIG. 3 illustrates a flowchart illustrating a first embodiment of the disclosed method of operating a consumable management system according to the present disclosure.

FIG. 3 illustrates the process carried out by the control unit 20, the method herein disclosed by way of a flowchart. Steps carried out in parallel or at different times, but independent of each other are illustrated in parallel, side-by-side process blocks.

In step 102, consumable demand can be captured by the interface 26.

In a step 104, the control unit 20 can determine the particular consumable 5 to be retrieved in accordance with the consumable demand and the inventory of consumables. According to a first embodiment, the control unit 20 can determine the particular consumable to be retrieved as the one of a plurality of similar/like consumables with a nearest shelf-life expiry, nearest expiry date and/or most accessible position in storage compartment 12. In one embodiment, these three considerations can be prioritized as listed above, that is, first a consumable 5 nearing shelf life expiry can be determined as next to be used. If no such consumable exists, then the consumable 5 can be chosen which will expire first. Between consumables 5 expiring at the same time, the consumable 5 which is most accessible (e.g., in the frontmost position of a compartment) can be determined as the particular consumable to be retrieved. In order to reduce storage space taken by almost used-up (empty) consumables 5, according to a further embodiment, the control unit 20 can determine the particular consumable to be retrieved as the one of a plurality of like consumables 5 which has been opened and has the least amount of left over quantity. Since expiry of partially used consumables 5 can be a cause of consumable waste, alternatively, or additionally, the control unit 20 can be configured to determine the particular consumable to be retrieved as the one of a plurality of like consumables which has been opened for the longest period of time. According to some embodiments, the control unit 20 can determine whether the remaining amount within a consumable 5 package can be sufficient to perform outstanding test orders requiring the consumable. If not sufficient, the control unit 20 can be configured to determine an alternative consumable 5 to be retrieved with sufficient remaining amount to perform outstanding test orders.

In a step 106, the control unit 20—based on the inventory of consumables in the database 30—can determine which storage compartment 12 can hold the particular consumable 5 (determined in step 104).

In a following step 108, the control unit 20 can control the plurality of compartment indicators 14 to indicate the storage compartment 12 holding the particular consumable to be retrieved—for example as illustrated by a solid black circle 15 on FIGS. 1, 2, 4 and 5.

In step 110, a consumable 5 can be removed from a storage compartment.

Turning now to steps related to consumable loading/replenishment, in step 112, consumable demand and consumable replenishment intent can be captured by the interface 26.

In step 114, the control unit 20 can determine the particular storage compartment 12 best suited to receive the consumable replenishment. According to various embodiments, the determination of the storage compartment 12 to receive the next consumable 5 may be based on a first in-first out (FIFO), a last in-first out (LIFO) or other suitable approaches, in each case taking in consideration the inventory of consumables. Thereafter, in a step 118, the control unit 20 can control the plurality of compartment indicators 14 to indicate the storage compartment 12 best suited to receive a consumable replenishment.

In step 120, a consumable 5 can be replenished into a storage compartment.

Parallel to the sequences of steps 102-110 respectively 112-120, in a step 130, the detection unit 40 can monitor removal and replenishment activities and transmit signals indicative thereof to the control unit 20. In subsequent step 140, the control unit 20 can process the signals from the detection unit 40 in order to validate removal of the particular consumable 5 from the storage compartment 12 indicated and replenishment into the storage compartment 12 indicated. Validation herein can refer to checking whether the user removed/replenished a consumable 5 from the indicated compartment 12. In other words, validation can verify actions of removal/replenishment—as detected by the detection unit 40—match the indication (user guidance) by the compartment indicators 14. If the validation fails, the control unit 20 can generate an alert in step 150. The alert may be an audible alert and/or a visual alert, e.g., by compartment indicator(s) 14 or by elements of a GUI. In addition, failed validation(s) can be recorded in the database 30.

In addition to monitoring which storage compartment(s) 12 consumables are removed from/replenished into, according to a further embodiment, the detection unit 40 can be further configured to identify the specific consumables 5 being removed or replenished into the consumable storage cluster 10 in order to:

validate the removal of the particular consumable 5 to be retrieved;

positively identify each replenished consumable 5 in order to update the inventory of consumables; and track ad-hoc consumable removal and/or consumable replenishment and correspondingly update the inventory of consumables, wherein consumable removal and/or consumable replenishment can be ad-hoc when no input indicative of a consumable demand and/or consumable replenishment intent can be received by the interface 26 related to the particular consumable 5 being removed/replenished.

Based on processing of the signals from the detection unit 40, in a step 100, the inventory of consumables can be updated.

Figure 4:
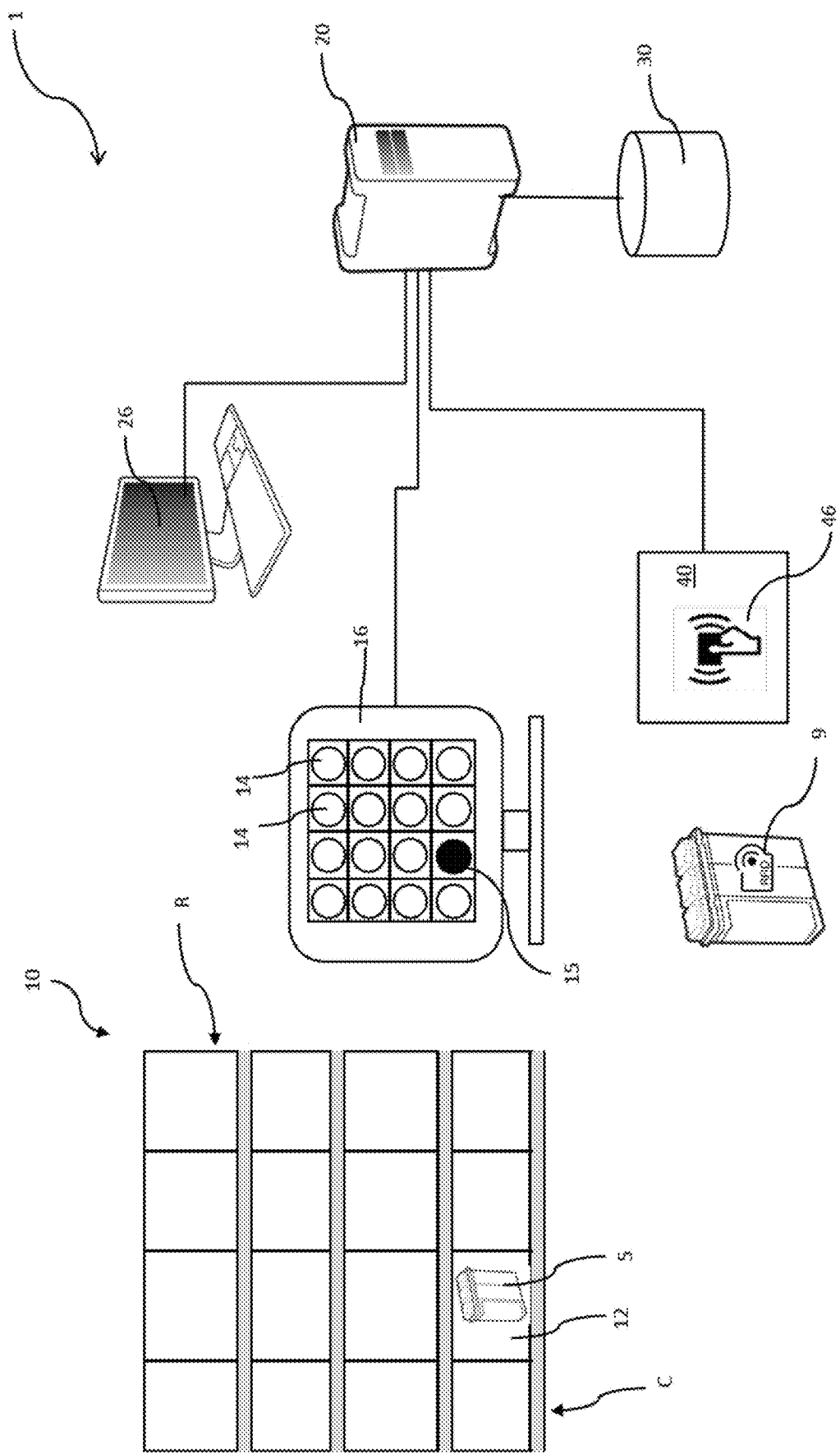
FIG. 4 illustrates a schematic diagram of a further embodiment of the disclosed consumable management system, wherein the plurality of compartment indicators comprises a plurality of visual elements of a graphical user interface GUI displayed on a computer screen according to the present disclosure.

FIG. 4 shows a further embodiment of the consumable management system 1. The plurality of compartment indicators 14 can comprise a plurality of visual elements 14 of a GUI displayed on a screen 16 communicatively connected to the control unit 20. The plurality of visual elements 14 can be arranged on the GUI to resemble the spatial arrangement of the plurality of storage compartments 12 of the consumable storage cluster 10. Additionally, or alternatively, the plurality of compartment indicators 14 can comprise a plurality of visual cues of an augmented reality interface. The plurality of visual cues can be projected as an overlay in the field of view of a user such as to overlay on the plurality of storage compartments 12 of the consumable storage cluster 10.

Also shown on FIG. 4, the consumable storage cluster 10 can be arranged as a two-dimensional raster of rows R respectively columns C. Furthermore, FIG. 4 shows an embodiment of the detection unit 40 comprising an RFID reader 46 such as, for example, a handheld RFID reader 46, configured to identify the consumables 5 being removed from and replenished into the consumable storage cluster 10. Alternatively, a barcode reader can be used for reading a barcode attached onto consumables 5.

Figure 5:
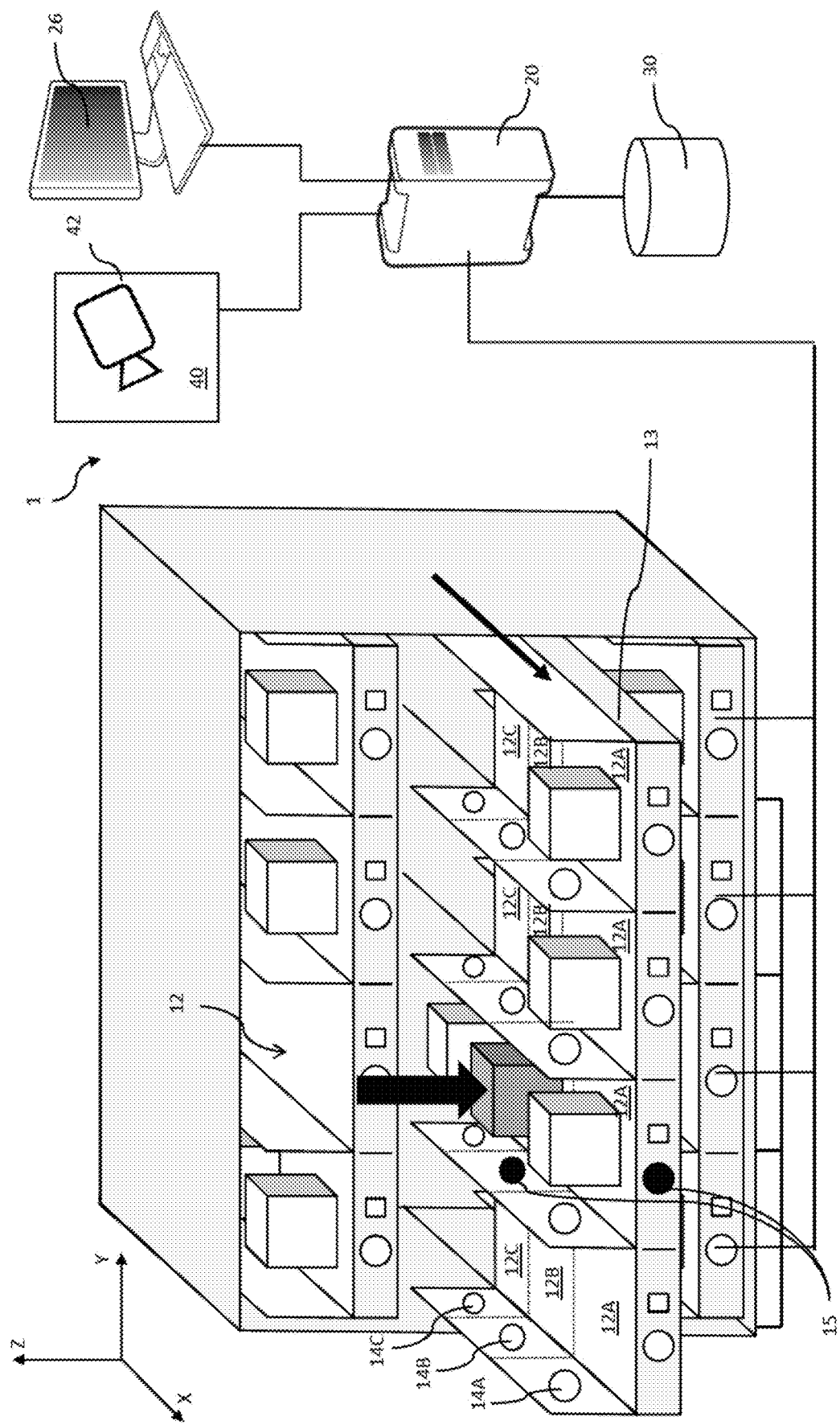
FIG. 5 illustrates a schematic diagram of a further embodiment of the disclosed consumable management system having extendable drawers allowing random access to consumables according to the present disclosure.

FIG. 5 shows an even further embodiment of the storage cluster 10 comprising one or more storage drawers 13. The drawers 13 can be arranged on top of each other and housed in an enclosure. Each drawer 13 can comprise one or more storage compartments 12 side-by-side along the Y-direction of the three-dimensional Cartesian coordinate system. As the name suggests, each drawer 13 can be configured to be extendable in the X-direction such as to allow random access to any consumable 5 within any storage compartment 12 of the drawer 13. Random access hereby can refer to the fact that a user can pick any consumable 5 from a storage compartment 12 without having to move any other in order to gain access—as opposed to only having access to the consumable 5 in front if it were not for the drawer 13. In the embodiment shown on FIG. 5, the storage compartments 12 of the drawers 13 can comprise storage compartment sections 12A, 12B, 12C arranged one behind the other (in the X-direction), with compartment section indicators 14A, 14B, 14C configured to indicate the respective storage compartment sections 12A, 12B, 12C. To control the compartment section indicators 14A, 14B, 14C, the control unit 20 can be configured to:

determine the storage compartment section 12A, 12B, 12C holding the particular consumable 5 to be retrieved and control the plurality of compartment section indicators 14A, 14B, 14C to indicate the storage compartment section 12A, 12B, 12C holding the particular consumable to be retrieved; and the control unit 20 is configured to determine the storage compartment section 12A, 12B, 12C best suited to receive the consumable replenishment and control the plurality of compartment section indicators 14A, 14B, 14C to indicate the storage compartment 12 best suited to receive a consumable replenishment.

Further disclosed and proposed is a computer program product including computer-executable instructions for performing the disclosed method in one or more of the embodiments enclosed herein when the program is executed on a computer or computer network. Specifically, the computer program may be stored on a computer-readable data carrier or a server computer. Thus, specifically, one, more than one or even all of method steps as indicated above may be performed by using a computer or a computer network, preferably by using a computer program.

As used herein, a computer program product refers to the program as a tradable product. The product may generally exist in any format, such as in a paper format, or on a computer-readable data carrier on premise or located at a remote location. Specifically, the computer program product may be distributed over a data network (such as a cloud environment). Furthermore, not only the computer program product, but also the execution hardware may be located on premise or in a cloud environment.

Further disclosed and proposed is a computer-readable medium comprising instructions which, when executed by a computer system, cause a laboratory system to perform the method according to one or more of the embodiments disclosed herein.

Further disclosed and proposed is a modulated data signal comprising instructions which, when executed by a computer system, cause a laboratory system to perform the method according to one or more of the embodiments disclosed herein.

Referring to the computer-implemented aspects of the disclosed method, one or more of the method steps or even all of the method steps of the method according to one or more of the embodiments disclosed herein may be performed by using a computer or computer network. Thus, generally, any of the method steps including provision and/or manipulation of data may be performed by using a computer or computer network. Generally, these method steps may include any of the method steps, typically except for method steps requiring manual work, such as providing the samples and/or certain aspects of performing the actual measurements.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. A consumable management system for laboratories, the consumable management system comprising:

a consumable storage cluster comprising a plurality of storage compartments, each storage compartment configured to receive one or more consumables, and a plurality of compartment indicators, a compartment indicator being associated with each storage compartment and configured to indicate one of the plurality of storage compartments to a user;

a control unit communicatively connected to a database for maintaining an inventory of consumables stored in the plurality of storage compartments, the database including records of at least one of the opening time, shelf life, or partial consumption of a particular consumable;

a detection unit communicatively connected with the control unit and configured to detect removal and replenishment of consumables from and into the storage compartments and signaling the removal and replenishment to the control unit; and an interface communicatively connected with the control unit for receiving an input indicative of a consumable demand and/or consumable replenishment intent, wherein the control unit is programmed and configured to:

based on the database records of consumables, determine a demand for the replenishment of the inventory, the demand for the replenishment of the inventory based on at least one of the opening time, shelf life, or partial consumption of a particular consumable, determine a particular consumable to be retrieved in accordance with the consumable demand and the inventory of consumables, determine the storage compartment holding the particular consumable to be retrieved and control the plurality of compartment indicators to indicate the storage compartment holding the particular consumable to be retrieved, based on the at least one of the opening time, shelf life, or partial consumption of the inventory of consumables, determine the particular storage compartment best suited to receive the consumable replenishment and control the plurality of compartment indicators to indicate the storage compartment best suited to receive a consumable replenishment, process signals from the detection unit in order to validate removal of the particular consumable from the storage compartment indicated and replenishment into the storage compartment indicated, generate an alert signal upon failure of the validation of the removal of the particular consumable from the storage compartment indicated and replenishment into the storage compartment indicated, and process signals from the detection unit in order to update the inventory of consumables upon removal and upon replenishment of consumables, wherein to determine the particular consumable to be retrieved in accordance with the consumable demand and the inventory of consumables, the control unit is configured to, in a priority order as follows with a highest priority item listed first and a lowest priority item listed last: (i) determine the particular consumable to be retrieved as the one of a plurality of like consumables with a nearest shelf life expiry, (ii) determine the particular consumable to be retrieved as the one of a plurality of like consumables with a nearest expiry date, and (iii) determine the particular consumable to be retrieved as the one of a plurality of like consumables with a most accessible position in a storage compartment, wherein the nearest shelf life expiry corresponds to a nearest expiration of a period of time during which the one of the plurality of like consumables may be stored without becoming unfit for use, wherein the nearest expiry date corresponds to a nearest point in time after which the one of the plurality of like consumables should no longer be used, and wherein to determine the particular consumable to be retrieved in accordance with the consumable demand and the inventory of consumables, the control unit is configured to: (a) first make the determination (i), then if no such determination is made, (b) make the determination (ii), and then if two or more of the plurality of like consumables are determined to have a same expiry date, (c) make the determination (iii) to retrieve the one of the plurality of like consumables with the most accessible position.

2. The consumable management system according to claim 1, wherein the control unit is configured to:

determine the particular consumable to be retrieved as the one of a plurality of like consumables which has been opened and has the least amount of left over quantity, and determine the particular consumable to be retrieved as the one of a plurality of like consumables which has been opened for the longest period of time.

3. The consumable management system according to claim 1, wherein the plurality of compartment indicators comprises a plurality of light sources as compartment indicators, each light source being arranged in the proximity of the respective storage compartment and/or the plurality of compartment indicators comprise a plurality of visual elements of a graphical user interface (GUI) displayed on a screen communicatively connected to the control unit, the plurality of visual elements being arranged on the GUI to resemble the spatial arrangement of the plurality of storage compartments of the consumable storage cluster and/or the plurality of compartment indicators comprise a plurality of visual cues of an augmented reality interface, the plurality of visual cues being projected as an overlay in the field of view of a user such as to overlay on the plurality of storage compartments of the consumable storage cluster.

4. The consumable management system according to claim 3, wherein the plurality of light sources comprises light emitting diodes (LEDs).

5. The consumable management system according to claim 1, wherein the detection unit comprises an optical data acquisition device arranged and configured such as to:

capture images of the consumable storage cluster and to detect the particular storage compartment(s) from which consumables are removed and respectively into which consumables are being replenished and/or capture images of labels attached to the consumables and detect whether the consumable being removed and replenished is the particular consumable determined by the control unit that must be removed/replenished.

6. The consumable management system according to claim 1, wherein the detection unit comprises a plurality of RFID tag readers, wherein each RFID tag reader of the plurality of RFID tag readers is associated with a respective storage compartment of the plurality of storage compartments and configured to read only RFID tags attached to consumables within the respective storage compartment being removed from or replenished into the consumable storage cluster such as to detect the particular storage compartment from which consumables are removed and into which consumables are being replenished.

7. The consumable management system according to claim 1, wherein the detection unit is further configured to identify the consumables being removed and being replenished into the consumable storage cluster in order to:

validate the removal of the particular consumable to be retrieved, positively identify each replenished consumable in order to update the inventory of consumables, and track ad-hoc consumable removal and/or consumable replenishment and correspondingly update the inventory of consumables, wherein consumable removal and/or consumable replenishment is ad-hoc when no input indicative of a consumable demand and/or consumable replenishment intent is received by the interface related to the particular consumable being removed/replenished.

8. The consumable management system according to claim 7, wherein in order to identify the consumables being removed from or being replenished into the consumable storage cluster, the detection unit comprises one or more of: an RFID tag reader configured to read an RFID tag attached to consumables and/or a barcode reader configured to read barcode attached to consumables.

9. The consumable management system according to claim 8, wherein the RFID tag reader is a handheld RFID tag reader.

10. The consumable management system according to claim 1, wherein the storage cluster comprises one or more storage drawers comprising one or more storage compartments side-by-side along the Y-direction of the three-dimensional Cartesian coordinate system, each drawer configured to be extendable in the X-direction of the three-dimensional Cartesian coordinate system such as to allow random access to any consumable within any storage compartment of the drawer.

11. The consumable management system according to claim 1, wherein the plurality of compartment indicators is configured to indicate a particular consumable located within the respective storage compartment and wherein the control unit is configured to control the plurality of compartment indicators to indicate the particular consumable to be retrieved.

12. The consumable management system according to claim 1, wherein one or more of the plurality of storage compartments comprise storage compartment sections, wherein the plurality of compartment indicators comprise compartment section indicators configured to indicate the respective storage compartment sections to a user, wherein the control unit is configured to determine the storage compartment section holding the particular consumable to be retrieved and control the plurality of compartment section indicators to indicate the storage compartment section holding the particular consumable to be retrieved, and wherein the control unit is configured to determine the storage compartment section best suited to receive the consumable replenishment and control the plurality of compartment section indicators to indicate the storage compartment section best suited to receive a consumable replenishment.

13. The consumable management system of claim 1 wherein the consumables comprise laboratory system elements designated for carrying out analytical laboratory tests.

14. The consumable management system of claim 13 wherein the laboratory system elements designated for carrying out analytical laboratory tests comprise at least one of reagents, quality control materials, calibration materials, and replaceable laboratory instrument parts.

15. A method of operating a consumable management system, the method comprising:
    maintaining an inventory of consumables stored in a plurality of storage compartments of a consumable storage cluster in a database communicatively connected to a control unit of the consumable management system, each storage compartment having a compartment indicator, the indicator being a light source, and the consumables comprising laboratory system elements designated for carrying out analytical laboratory tests;
    receiving an input indicative of a consumable demand and a consumable replenishment intent via an interface communicatively connected with the control unit;
    based on the database records of consumables, determining a demand for the replenishment of the inventory of consumables;
    determining a particular consumable to be retrieved in accordance with the consumable demand and the inventory of consumables by the control unit;
    determining by the control unit the storage compartment holding the particular consumable to be retrieved and controlling the plurality of compartment indicators;
    indicating the storage compartment holding the particular consumable to be retrieved by one of the plurality of compartment indicators;
    based on the determined demand for the replenishment of the inventory of consumables, determining by the control unit the particular storage compartment best suited to receive the consumable replenishment;
    indicating the storage compartment best suited to receive a consumable replenishment by one of the plurality of compartment indicators;
    replenishing and removing one or more consumables into and from one of the plurality of storage compartments;
    detecting removal and replenishment of consumables from and into the storage compartments by a detection unit and signaling the removal and replenishment to the control unit;
    processing signals from the detection unit by the control unit and validating removal of the particular consumable from the storage compartment indicated and replenishment into the storage compartment indicated; and
    generating an alert signal using one of the plurality of compartment indicators or an audio alarm upon failure of the validation of the removal of the particular consumable from the storage compartment indicated and replenishment into the storage compartment indicated,
    wherein determining the particular consumable to be retrieved in accordance with the consumable demand and the inventory of consumables by the control unit comprises, in a priority order as follows with a highest priority item listed first and a lowest priority item listed last: (i) determining the particular consumable to be retrieved as the one of a plurality of like consumables with a nearest shelf life expiry, (ii) determining the particular consumable to be retrieved as the one of a plurality of like consumables with a nearest expiry date, and (iii) determining the particular consumable to be retrieved as the one of a plurality of like consumables with a most accessible position in a storage compartment,
    wherein the nearest shelf life expiry corresponds to a nearest expiration of a period of time over which the one of the plurality of like consumables may be stored without becoming unfit for use,
    wherein the nearest expiry date corresponds to a nearest point in time after which the one of the plurality of like consumables should no longer be used,
    wherein to determine the particular consumable to be retrieved in accordance with the consumable demand and the inventory of consumables, the control unit is configured to: (a) first make the determination (i), then if no such determination is made, (b) make the determination (ii), and then if two or more of the plurality of like consumables are determined to have a same expiry date, (c) make the determination (iii) to retrieve the one of the plurality of like consumables with the most accessible position, and
    wherein to determine the particular consumable to be retrieved in accordance with the consumable demand and the inventory of consumables in an event the particular consumable is not determined according to determinations (i)-(iii), the control unit is configured to then (iv) determine the particular consumable to be retrieved as the one of a plurality of like consumables which has been opened and has the least amount of left over quantity, and then if no such determination is made, (v) determine the particular consumable to be retrieved as the one of a plurality of like consumables which has been opened for the longest period of time.

16. The method according to claim 13, further comprising,
    capturing images of the consumable storage cluster by an optical data acquisition device of the detection unit; and
    detecting the particular storage compartment from which consumables are removed and into which consumables are replenished.

17. The method according to claim 14, further comprising,
    capturing images of labels attached to the consumables; and
    detecting whether the consumable being removed and being replenished is the particular consumable determined by the control unit that must be removed and replenished, respectively.

18. The method according to claim 17, further comprising,
    reading an RFID tag attached to consumables being removed from and being replenished into the consumable storage cluster by one of a plurality of RFID tag readers, an RFID tag reader being associated with each storage compartment; and detecting the particular storage compartment from which consumables are removed and into which consumables are being replenished.

19. A non-transitory computer readable medium storing a computer program product comprising instructions which when executed by the control unit of the consumable management system cause the control unit to carry out the method according to claim 15.

20. The method of claim 15 wherein the database includes records of at least one of the opening time, shelf life, or partial consumption of particular consumables and wherein the demand for the replenishment of the inventory is based on the records of the at least one of the opening time, shelf life, or partial consumption of particular consumables.

* * * * *